(12) United States Patent
Flaherty et al.

(10) Patent No.: US 7,751,877 B2
(45) Date of Patent: Jul. 6, 2010

(54) NEURAL INTERFACE SYSTEM WITH EMBEDDED ID

(75) Inventors: J. Christopher Flaherty, Topsfield, MA (US); L. Renée Capachione, Acton, MA (US); Daniel S. Morris, Stanford, CA (US); Abraham H. Caplan, Cambridge, MA (US); Maryam Saleh, Providence, RI (US); K. Shane Guillory, Salt Lake City, UT (US)

(73) Assignee: BrainGate Co., LLC, Ponte Vedra Beach, FL (US)

( * ) Notice: Subject to any disclaimer, the term of this patent is extended or adjusted under 35 U.S.C. 154(b) by 1484 days.

(21) Appl. No.: 10/992,111

(22) Filed: Nov. 19, 2004

(65) Prior Publication Data

US 2005/0267597 A1 Dec. 1, 2005

Related U.S. Application Data

(60) Provisional application No. 60/524,969, filed on Nov. 25, 2003.

(51) Int. Cl.
*A61B 5/00* (2006.01)
(52) U.S. Cl. ...................................................... 600/544
(58) Field of Classification Search ........................ None
See application file for complete search history.

(56) References Cited

U.S. PATENT DOCUMENTS

| | | | |
|---|---|---|---|
| 3,837,339 A | 9/1974 | Aisenberg et al. |
| 3,850,161 A | 11/1974 | Liss |
| 4,055,175 A | 10/1977 | Clemens et al. |
| 4,146,029 A | 3/1979 | Ellinwood, Jr. |
| 4,294,245 A | 10/1981 | Bussey |
| 4,360,031 A | 11/1982 | White |
| 4,461,304 A | 7/1984 | Kuperstein |
| 4,633,889 A | 1/1987 | Talalla et al. |

(Continued)

FOREIGN PATENT DOCUMENTS

WO WO 01/43635 6/2001

(Continued)

OTHER PUBLICATIONS

Kensall D. Wise et al., "An Integrated-Circuit Approach to Extraceullar Microelectrodes," IEEE Transactions on Biomedical Engineering, vol. BME-17, No. 3, Jul. 1970, pp. 238-247.

(Continued)

*Primary Examiner*—Robert L Nasser
(74) *Attorney, Agent, or Firm*—SoCal IP Law Group LLP; Steven C. Sereboff; M. Kala Sarvaiya

(57) ABSTRACT

A system and method for a neural interface system with a unique identification code includes a sensor including a plurality of electrodes to detect multicellular signals, an processing unit to process the signals from the sensor into a suitable control signal for a controllable device such as a computer or prosthetic limb. The unique identification code is embedded in one or more discrete components of the system. Internal and external system checks for compatibility and methods of ensuring safe and effective performance of a system with detachable components are also disclosed.

14 Claims, 4 Drawing Sheets

U.S. PATENT DOCUMENTS

| | | |
|---|---|---|
| 4,690,142 A | 9/1987 | Ross et al. |
| 4,837,049 A | 6/1989 | Byers et al. |
| 4,865,048 A | 9/1989 | Eckerson |
| 4,878,913 A | 11/1989 | Aebischer et al. |
| 4,883,666 A | 11/1989 | Sabel et al. |
| 4,969,468 A | 11/1990 | Byers et al. |
| 5,037,376 A | 8/1991 | Richmond et al. |
| 5,081,990 A | 1/1992 | Deletis |
| 5,119,832 A | 6/1992 | Xavier |
| 5,156,844 A | 10/1992 | Aebischer et al. |
| 5,215,088 A | 6/1993 | Normann et al. |
| 5,325,862 A * | 7/1994 | Lewis et al. ................ 600/544 |
| 5,325,865 A | 7/1994 | Beckman et al. |
| 5,361,760 A | 11/1994 | Normann et al. |
| 5,423,877 A | 6/1995 | Mackey |
| 5,445,608 A | 8/1995 | Chen et al. |
| 5,458,631 A | 10/1995 | Xavier |
| 5,474,547 A | 12/1995 | Aebischer et al. |
| 5,617,871 A | 4/1997 | Burrows |
| 5,638,826 A | 6/1997 | Wolpaw et al. |
| 5,687,291 A | 11/1997 | Smyth |
| 5,692,517 A | 12/1997 | Junker |
| 5,697,951 A | 12/1997 | Harpstead et al. |
| 5,702,432 A | 12/1997 | Chen et al. |
| 5,713,923 A | 2/1998 | Ward et al. |
| 5,735,885 A | 4/1998 | Howard, III et al. |
| 5,758,651 A | 6/1998 | Nygard et al. |
| 5,797,898 A | 8/1998 | Santini, Jr. et al. |
| 5,814,089 A | 9/1998 | Stokes et al. |
| 5,843,093 A | 12/1998 | Howard, III |
| 5,843,142 A | 12/1998 | Sultan |
| 5,855,801 A | 1/1999 | Lin et al. |
| 5,873,840 A | 2/1999 | Neff |
| 5,928,228 A | 7/1999 | Kordis et al. |
| 5,938,688 A | 8/1999 | Schiff |
| 5,938,689 A | 8/1999 | Fischell et al. |
| 5,938,690 A | 8/1999 | Law et al. |
| 6,001,065 A | 12/1999 | DeVito |
| 6,006,124 A | 12/1999 | Fischell et al. |
| 6,016,449 A | 1/2000 | Fischell et al. |
| 6,024,700 A | 2/2000 | Nemirovski et al. |
| 6,024,702 A | 2/2000 | Iversen |
| 6,027,456 A | 2/2000 | Feler et al. |
| 6,038,477 A | 3/2000 | Kayyali |
| 6,061,593 A | 5/2000 | Fischell et al. |
| 6,086,582 A | 7/2000 | Altman et al. |
| 6,091,015 A | 7/2000 | del Valle et al. |
| 6,092,058 A | 7/2000 | Smyth |
| 6,113,553 A | 9/2000 | Chubbuck |
| 6,125,300 A | 9/2000 | Weijand et al. |
| 6,128,538 A | 10/2000 | Fischell et al. |
| 6,134,474 A | 10/2000 | Fischell et al. |
| 6,154,678 A | 11/2000 | Lauro |
| 6,161,045 A | 12/2000 | Fischell et al. |
| 6,163,725 A | 12/2000 | Peckham et al. |
| 6,169,981 B1 | 1/2001 | Werbos |
| 6,171,239 B1 | 1/2001 | Humphrey |
| 6,175,762 B1 | 1/2001 | Kirkup et al. |
| 6,181,965 B1 | 1/2001 | Loeb et al. |
| 6,185,455 B1 | 2/2001 | Loeb et al. |
| 6,216,045 B1 | 4/2001 | Black et al. |
| 6,224,549 B1 | 5/2001 | Drongelen |
| 6,240,315 B1 | 5/2001 | Mo et al. |
| 6,254,536 B1 | 7/2001 | DeVito |
| 6,263,237 B1 | 7/2001 | Rise |
| 6,280,394 B1 | 8/2001 | Maloney et al. |
| 6,309,410 B1 | 10/2001 | Kuzma et al. |
| 6,313,093 B1 | 11/2001 | Frey, II |
| 6,319,241 B1 | 11/2001 | King et al. |
| 6,353,754 B1 | 3/2002 | Fischell et al. |
| 6,354,299 B1 | 3/2002 | Fischell et al. |
| 6,356,784 B1 | 3/2002 | Lozano et al. |
| 6,358,202 B1 | 3/2002 | Arent |
| 6,360,122 B1 | 3/2002 | Fischell et al. |
| 6,427,086 B1 | 7/2002 | Fischell et al. |
| 6,436,708 B1 | 8/2002 | Leone et al. |
| 6,459,936 B2 | 10/2002 | Fischell et al. |
| 6,466,822 B1 | 10/2002 | Pless |
| 6,473,639 B1 | 10/2002 | Fischell et al. |
| 6,480,743 B1 | 11/2002 | Kirkpatrick et al. |
| 6,577,893 B1 | 6/2003 | Besson et al. |
| 6,620,415 B2 | 9/2003 | Donovan |
| 2001/0023368 A1 | 9/2001 | Black et al. |
| 2001/0027336 A1 | 10/2001 | Gielen et al. |
| 2001/0029391 A1 | 10/2001 | Gluckman et al. |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0013612 A1 | 1/2002 | Whitehurst |
| 2002/0016638 A1 | 2/2002 | Mitra et al. |
| 2002/0077620 A1 | 6/2002 | Sweeney et al. |
| 2002/0099412 A1 | 7/2002 | Fischell et al. |
| 2002/0169485 A1 | 11/2002 | Pless et al. |
| 2003/0082507 A1 | 5/2003 | Stypulkowski |
| 2003/0083716 A1 | 5/2003 | Nicolelis et al. |
| 2003/0093129 A1 | 5/2003 | Nicolelis et al. |

FOREIGN PATENT DOCUMENTS

| | | |
|---|---|---|
| WO | WO 01/93756 A2 | 12/2001 |
| WO | WO 02/093312 A2 | 11/2002 |
| WO | WO 02/100267 A1 | 12/2002 |
| WO | WO 03/035165 | 5/2003 |
| WO | WO 03/037231 | 5/2003 |
| WO | WO 03/061465 A2 | 7/2003 |

OTHER PUBLICATIONS

Donald R. Humphrey et al., "Predicting Measures of Motor Performance from Multiple Cortical Spike Trains," Science, New Series, vol. 170, Issue 3959, Nov. 13, 1970, pp. 758-762.

A. Bohg, "Ethylene Diamine-Pyrocatechol-Water Mixture Shows Etching Anomaly in Boron-Doped Silicon," Journal of the Electrochemical Society, vol. 118, No. 2, Feb. 1971, pp. 401-402.

Donald R. Humphrey, "Relating Motor Cortex Spike Trains to Measures of Motor Performance," Department of Physiology, Emory University, Brain Research, No. 40, 1972, pp. 7-18.

Arnold Starr et al., "An Evaluation of Photoengraved Microelectrodes for Extracellular Single-Unit Recording," IEEE Transactions on Biomedical Engineering, vol. BME-20, No. 4, Jul. 1973, pp. 291-293.

Kensall D. Wise et al., "A Low-Capacitance Multielectrode Probe for Use in Extracellular Neurophysiology," IEEE Transactions on Biomedical Engineering, vol. BME-22, No. 3, May 1975, pp. 212-219.

V. B. Mountcastle et al., "Posterior Parietal Association Cortex of the Monkey: Command Functions for Operations Within Extrapersonal Space," The Journal of Neurophysiology, vol. 38, No. 4, 1975, pp. 871-908.

Edward M. Schmidt, "Single Neuron Recording From Motor Cortex as a Possible Source of Signals for Control of External Devices," Annals of Biomedical Engineering, vol. 8, 1980, pp. 339-349.

A. J. S. Summerlee et al., "The effect of behavioural arousal on the activity of hypothalamic neurons in unanaesthetized, freely moving rats and rabbits," Proceedings of the Royal Society of London Series B- Biological Sciences, Jan. 1982, pp. 263-272.

Spencer L. BeMent, et al., "Solid-State Electrodes for Multichannel Multiplexed Intracortical Neuronal Recording," IEEE Transactions on Biomedical Engineering, vol. BME-33, No. 2, Feb. 1986, pp. 230-241.

Camilo Toro et al., "8-12 Hz rhythmic oscillations in human motor cortex during two-dimensional arm movements: evidence for representation of kinematic parameters," Departments of Neurology, Neurosurgery, and Physiology, University of Minnesota; MINCEP Epilepsy Care, P.A.; The Minnesota Epilepsy Group of United and St. Paul Children's Hospital; and Human Motor Control Section, National Institute of Neurological Disorders and Stroke, National Institutes of Health, Electroencephalorapy and Clinical Neurophysiology, No. 93, 1994, pp. 390-403.

Anthony L. Owens et al., "Multi-electrode array for measuring evoked potentials from surface of ferret primary auditory cortex," Journal of Neuroscience Methods, vol. 58, Nos. ½, May 1995, pp. 209-220.

Miguel A. L. Nicolelis et al., "Sensorimotor Encoding by Synchronous Neural Ensemble Activity at Multiple Levels of the Somatosensory System," Science, vol. 268, Jun. 2, 1995, pp. 1353-1358.

Jerome N. Sanes et al., "Shared Neural Substrates Controlling Hand Movements in Human Motor Cortex," Science, vol. 268, Jun. 23, 1995, pp. 1775-1777.

D.M. Halliday et al., "A Framework for the Analysis of Mixed Time Series/Point Process Data-Theory and Application to the Study of Physiological Tremor, Single Motor Unit Discharges and Electromyograms," Progress in Biophysics Molecular Biology, vol. 64, Nos. 2/3, 1995, pp. 237-278.

Qing Bai et al., "A High-Yield Process for Three-Dimensional Microelectrode Arrays," Solid-State Sensor and Actuator Workshop, Hilton Head, South Carolina, Jun. 2-6, 1996, pp. 262-265.

Apostolos P. Georgopoulos et al., "Neuronal Population Coding of Movement Direction," Science, vol. 233, Sep. 26, 1986, pp. 1416-1419.

Kenneth L. Drake et al., "Performance of Planar Multisite Microprobes in Recording Extracellular Single-Unit Intracortical Activity," IEEE Transactions on Biomedical Engineering, vol. 35, No. 9, Sep. 1988, pp. 719-732.

Patrick K. Campbell et al., "A chronic intracortical electrode array: Preliminary results," Journal of Biomed. Material Res.: Applied Biomaterials, vol. 23, No. 2, 1989, pp. 245-259.

Andrew R. Mitz et al., "Learning-dependent Neuronal Activity in the Premotor Cortex: Activity during the Acquisition of Conditional Motor Associations," The Journal of Neuroscience, vol. 11, No. 6, Jun. 1991, pp. 1855-1872.

Patrick K. Campbell et al., "A Silicon-Based, Three-Dimensional Neural Interface: Manufacturing Processes for an Intracortical Electrode Array," IEEE Transactions, 1991, pp. 758-768.

A. C. Hoogerwerf et al., "A Three-Dimensional Neural Recording Array," IEEE Transactions, 1991, pp. 120-123.

Gregory T. A. Kovacs et al., "Regeneration Microelectrode Array for Peripheral Nerve Recording and Stimulation," Transactions on Biomedical Engineering, vol. 39, No. 9, Sep. 1992, pp. 893-902.

Kelly E. Jones et al., "A Glass/Silicon Composite Intracortical Electrode Array," Annals of Biomedical Engineering. vol. 20, 1992, pp. 423-437.

Miguel A. L. Nicolelis et al., "Induction of immediate spatiotemporal changes in thalamic networks by peripheral block of ascending cutaneous information," Letters to Nature, vol. 361, Feb. 11, 1993, pp. 533-536.

Reinhard Eckhorn et al., "A new method for the insertion of multiple microprobes into neural and muscular tissue, including fiber electrodes, fine wires, needles and microsensors," Journal of Neuroscience Methods, vol. 49, Nos. 1/2, 1993, pp. 175-179.

Craig T. Nordhausen et al., "Optimizing recording capabilities of the Utah Intracortical Electrode Array," Brain Research, vol. 637, Nos. 1/2 , Feb. 21, 1994, pp. 27-36.

Jamille F. Hetke et al., "Silicon Ribbon Cables for Chronically Implantable Microelectrode Arrays," IEEE Transactions on Biomedical Engineering, vol. 41, No. 4, Apr. 1994, pp. 314-321.

Miguel A. L. Nicolelis et al., "Spatiotemporal Structure of Somatosensory Responses of Many-Neuron Ensembles in the Rat Ventral PosteriorMedial Nucleus of the Thalamus," The Journal of Neuroscience, vol. 14, No. 6, Jun. 1994, pp. 3511-3532.

Arnold C. Hoogerwerf et al., "A Three-Dimensional Microelectrode Array for Chronic Neural Recording," IEEE Transactions on Biomedical Engineering, vol. 41, No. 12, Dec. 1994, pp. 1136-1146.

Changhyun Kim et al., "A 64-Site Multishank CMOS Low-Profile Neural Stimulating Probe," IEEE Journal of Solid-State Circuits, vol. 31, No. 9, Sep. 1996, pp. 1230-1238.

Gwo-Ching Chang et al., "Real-time implementation of electromyogram pattern recognition as a control command of man-machine interface," Medical Engineering Phys., vol. 18, No. 7, 1996, pp. 529-537.

P. Nisbet, "intergrating assistive technologies: current practices and future possibilities," Med. Eng. Phys., vol. 18, No. 3, 1996, pp. 193-202.

Miguel A. L. Nicolelis et al., "Reconstructing the Engram: Simultaneous, Multisite, Many Sinle Neuron Recordings," Nueron, vol. 18, Apr. 1997, pp. 529-537.

TR Scott et al., "The Monitoring of Tendon Tension with an Implantable Intratendon Probe and Its Use in the Control of Neuroprostheses," IEEE Transactions on Rehabilitation Engineering, vol. 5, No. 2, Jun. 1997, pp. 233-235.

Barbara M. Faggin et al., "Immediate and simultaneous sensory reorganization at cortical and subcortical levels of the somatosensory system," Proc. Natl. Acad. Science USA, vol. 94, Aug. 1997, pp. 9428-9433.

Nicolelis, Miguel A.L., "Trigeminal System Plasticity During Facial Anethesia," Department of Health and Human Services, Public Health Service, Grant No. 2 R01 DE11451-05, Including Summary Statement, Oct. 1997.

Robert M. Bradley et al., "Long term chronic recordings from peripheral sensory fibers using a sieve electrode array," Journal of Neuroscience Methods, vol. 73, 1997, pp. 177-186.

David K. Warland et al., "Decoding Visual Information From a Population of Retinal Ganglion Cells," The American Physiological Society, 1997, pp. 2336-2350.

Steven P. Wise et al., "Premotor and Parietal Cortex: Cortiococortical Connectivity and Combinatorial Computations," Annual Review of Neuroscience, vol. 20, 1997, pp. 25-42.

P.R. Kennedy et al., "Restoration of neural output from a paralyzed patient by a direct brain connection," NeuroReport, vol. 9, No. 8, Jun. 1998 pp. 1707-1711.

Paolo Dario et al., "Neural Interfaces for Regenerated Nerve Stimulation and Recording," IEEE Transactions on Rehabilitation Engineering, vol. 6, No. 4, Dec. 1998, pp. 353-363.

Nicholas G. Hatsopoulos et al., "Information about movement direction obtained from synchronous activity of motor cortical neurons," Proc. Natl. Acad. Sci. USA, vol. 95, Dec. 1998, pp. 15706-15711.

John P. Donoghue et al., "Neural Discharge and Local Field Potential Oscillations in Primate Motor Cortex During Voluntary Movements," The American Physiological Society, 1998, pp. 159-173.

Nicolelis, Miguel A.L., "Trigeminal System Plasticity During Facial Anethesia," Department of Health and Human Services, Public Health Service, Grant No. 2 R01 DE11451-06, Apr. 1999.

Gregor Rainer et al., "Prospective Coding for Objects in Primate Prefrontal Cortex," The Journal of Neuroscience, vol. 19, No. 13, Jul. 1, 1999, pp. 5493-5505.

John K. Chapin et al., "Real-time control of a robot arm using simultaneously recorded neurons in the motor cortex," Department of Neurobiology and Anatomy, MCP Hahnemann School of Medicine; and Department of Neurobiology, Duke University Medical Center, Nature Neuroscience, vol. 2, No. 7, Jul. 1999, pp. 664-670.

E. M. Maynard et al, "Neuronal Interactions Improve Cortical Population Coding of Movement Direction," The journal of Neuroscience, vol. 19, No. 18, Sep. 15, 1999, pp. 8083-8093.

F. Gandolfo et al., "Cortical correlates of learning in monkeys adapting to a new dynamical environment," PNAS, vol. 97, No. 5, Feb. 29, 2000, pp. 2259-2263.

J. F. Marsden et al., "Organization of Cortical Activities Related to Movement in humans," The Journal of Neuroscience, vol. 20, No. 6, Mar. 15, 2000, pp. 2307-2314.

D. Gareth Evans et al., "Controlling mouse Pointer Position Using an Infrared Head-Operated Joystick," IEEE Transaction on Rehabilitation Engineering, vol. 8, No. 1, Mar. 2000, pp. 107-117.

Qing Bai et al., "A High-Yield Microassembly Structure For Three-Dimensional Microelectrode Arrays," IEEE Transactions on Biomedical Engineering, vol. 47, No. 3, Mar. 2000, pp. 281-289.

Nicolelis, Miguel A.L., "Trigeminal System Plasticity During Facial Anethesia," Department of Health and Human Services, Public health Service, Grant No. 2 R01 DE11451-07, Apr. 2000.

Nicolelis, Miguel A.L., "Corticofugal Modulation of Tactile Sensory Processing," Department of Health and Human Services, Public Health Service, National Institute of Dental and Craniofacial Research of the Nationsl Institutes of health, Grant No. 1 R01 DE013810-01 A1, Jun. 2000.

Jonathan R. Wolpaw et al., "Brain-Computer Interface Technology: A Review of the First International Meeting," IEEE Transactions on Rehabilitation Engineering, vol. 8, No. 2, Jun. 2000, pp. 164-173.

Simon P. Levine et al., "A Direct Brain Interface Based on Event-Related potentials," IEEE Transactions on Rehabilitation Engineering, vol. 8, No. 2, Jun. 2000, pp. 180-185.

Robert E. Isaacs et al., "Work Toward Real-Time Control of a cortical Neural Prothesis," IEEE Transactions on Rehabilitation Engineering, vol. 8, No. 2, Jun. 2000, pp. 196-198.

Scott Makeig et al., A Natural Basis for Efficient Brain-Actuated Control, IEEE Transactions on Rehabilitation Engineering, vol. 8, No. 2, Jun. 2000, pp. 208-211.

Johan Wessberg et al., "Real-time prediction of hand trajectory by ensembles of cortical neurons in primates," Nature, vol. 408, Nov. 16, 2000, pp. 361-365.

Jerome N. Sanes et al., "Plasticity and Primary Motor Cortex," Annual Reviews, Neuroscience, Brown University, Library, vol. 23, 2000, pp. 393-415.

Jonathan C. Jarvis et al., "The application and technology of implantable neuromuscular stimulators: an introduction and overview," Medical Engineering & Physics, No. 23, Jan. 11, 2001, pp. 3-7.

Miguel A. L. Nicolelis, "Real-time direct interfaces between the brain and electronic and mechanical devices could one day be used to restore sensory and motor functions lost through injury or disease. Hybrid brain-machine interfaces also have the potential to enhance our perceptual, motor and cognitive capabilities by revolutionizing the way we use computers and interact with remote environments," Nature, vol. 409, Jan. 18, 2001, pp. 403-407.

Gerald E. Loeb et al., "BION™ system for distributed neural prosthetic interfaces," Medical Engineering & Physics, vol. 23, Jan. 26, 2001, pp. 9-18.

Patrick J. Rousche et al., "Flexible Polyimide-Based Intracortical Electrode Arrays with Bioactive Capability," IEEE Transactions on Biomedical Engineering, vol. 48, No. 3, Mar. 2001, pp. 361-371.

Nicolelis, Miguel A.L., "Trigeminal System Plasticity During Facial Anethesia," Department of Health and Human Services, Public Health Service, Grant No. 2 R01 DE11451-08, Apr. 2001.

Qing Bai et al., "Single-Unit Neural Recording with Active Microelectrode Arrays," IEEE Transactions on Biomedical Engineering, vol. 48, No. 8, Aug. 2001, pp. 911-920.

David L. Zealear et al., "The Biocompatibility, Integrity, and Positional Stability of an Injectable Microstimulator for Reanimation of the Paralyzed Larynx," IEEE Transactions on Biomedical Engineering, vol. 48, No. 8, Aug. 2001, pp. 890-897.

Dawn M. Taylor et al., "Using Virtual Reality to Test the Feasibility of Controlling an Upper Limb Fes System Directly from Multiunit Activity in the Motor Cortex," Arizona State University; and The Neurosciences Institute, Summer 2001, pp. 1-3.

Ranu Jung et al., "Real-Time Interaction Between a Neuromorphic Electronic Circuit and the Spinal Cord," IEEE Transactions on Neural Systems and Rehabilitation Engineering, vol. 9, No. 3, Sep. 2001, pp. 319-326.

Shay Shoham, "Advances Towards an Implantable Motor Cortical Interface," The University of Utah, Dec. 2001, pp. 1-157.

John K. Chapin et al., "Neural Prostheses for Restoration of Sensory and Motor Function," CRC Press, LLC, 2001, Chapters 6, 8 and 9 pp. 179-219, pp. 235-261, pp. 263-283.

Andrew B. Schwartz et al., "Extraction algorithms for cortical control of arm prosthetics," The Neuroscience Institute; and Department of Bioengineering, Arizona State University, 2001, pp. 701-707.

István Ulbert et al., "Multiple microelectrode-recording system for human intracortical applications," Journal of Neuroscience Methods, vol. 106, 2001, pp. 69-79.

Mijail D. Serruya et al., "Instant Neural Control of a Movement Signal," Nature, vol. 416, Mar. 14, 2002, pp. 141-142.

Nicolelis, Miguel A.L., "Corticofugal Modulation of Tactile Sensory Processing," Department of Health and Human Services, Public health Service, National Institute of Dental and Craniofacial Research of the Nationsl Institutes of Health, Grant No. 5 R01 DE013810-02, Mar. 2002.

Nicolelis, Miguel A.L., "Trigeminal System Plasticity During Facial Anethesia," Department of Health and Human Services, Public Health Service, Grant No. 2 R01 DE11451-09, Apr. 2002.

Dawn M. Taylor et al., "Direct Cortical Control of 3D Neuroprosthetic Devices," Science, vol. 296, Jun. 7, 2002, pp. 1829-1832.

John P. Donoghue, "Connecting cortex to machines: recent advances in brain interfaces," Nature Neuroscience Supplement, vol. 5, Nov. 2002, pp. 1085-1088.

Y. Gao, et al., "Probabilistic Inference of Hand Motion from Neural Activity in Motor Cortex," in Advances in Neural Information Processing Systems 14, The MIT Press, 2002, pp. 1-8.

Mijail Serruya et al., "Robustness of neuroprosthetic decoding algorithms," Biological Cybernetics, 2003, pp. 1-10.

Frank Wood et al., "On the Variability of Manual Spike Sorting," Brown University, Providence, RI, Jul. 1, 2003, pp. 1-19.

Wei Wu et al., "Modeling and Decoding Motor Cortical Activity using a Switching Kalman Filter,"Brown University, Providence, RI, Jul. 1, 2003, pp. 1-30.

Jose M. Carmena et al., "Learning to Control a Brain-Machine Interface for Reaching and Grasping by Primates," PLOS Biology, vol. 1, Issue 2, Oct. 13, 2003, pp. 1-16.

Nicolelis, Miguel A.L., "Brain-machine Interfaces to Restore Motor Function and Probe Neural Circuits," Nature Reviews, Neuroscience, vol. 4, May 2003, pp. 417-422.

Libet, Benjamin, "Unconscious Cerebral Initiative and the Role of Conscious Will in Voluntary Action," The Behavioral and Brain Sciences 1995) 8, pp. 529-566.

* cited by examiner

NEURAL INTERFACE SYSTEM WITH
EMBEDDED ID

This application claims the benefit of priority under 35 U.S.C. §119(e) of U.S. provisional application No. 60/524,969, filed Nov. 25, 2003.

FIELD OF THE INVENTION

The present invention relates to neural interface systems with unique embedded identifiers, and, more particularly, to systems and methods whereby a neural interface system utilizes the unique embedded electronic signature or identifier to assure compatibility of a multiple component system.

DESCRIPTION OF RELATED ART

Neural interface devices are currently under development for numerous applications including restoration of lost function due to traumatic injury or neurological disease. Sensors, such as electrode arrays, implanted in the higher brain regions that control voluntary movement can be activated voluntarily to generate electrical signals that can be processed by a neural interface device to create a thought invoked control signal. Such control signals can be used to control numerous devices including computers and communication devices, external prostheses, such as an artificial arm or functional electrical stimulation of paralyzed muscles, as well as robots and other remote control devices. Patient's afflicted with amyotrophic lateral sclerosis (Lou Gehrig's Disease), particularly those in advanced stages of the disease, would also be applicable to receiving a neural interface device, even if just to improve communication to the external world and thus improve their quality of life.

Early attempts to utilize signals directly from neurons to control an external prosthesis encountered a number of technical difficulties. The ability to identify and obtain stable electrical signals of adequate amplitude was a major issue. Another problem that has been encountered is caused by the changes that occur to the neural signals that occur over time, resulting in a degradation of system performance. Neural interface systems that utilize other neural information, such as electrocorticogram (ECOG) signals, local field potentials (LFPs) and electroencephalogram (EEG) signals have similar issues to those associated with individual neuron signals. Since all of these signals result from the activation of large groups of neurons, the specificity and resolution of the control signal that can be obtained is limited. However, if these lower resolution signals could be properly identified and the system adapt to their changes over time, simple control signals could be generated to control rudimentary devices or work in conjunction with the higher power control signals processed directly from individual neurons.

Commercialization of these neural interfaces has been extremely limited, with the majority of advances made by universities in a preclinical research setting. As the technologies advance and mature, the natural progression will be to sophisticated human applications, such as those types of devices regulated by various governmental regulatory agencies including the Food and Drug Administration in the United States. When sophisticated neural interface systems are commercially available for prescription by an appropriate clinician, it will become very important for these devices to include numerous safety features required in the hospital and home health care settings. Systems which perform component compatibility, software compatibility and other checks of safe and effective performance may be necessary.

There is therefore a need for an improved neural interface system which incorporates hardware and/or software embodiments which may confirm safe and effective performance of the system. Performance of these safety checks at specific events and repeated periodically throughout the life of the system would ensure a sophisticated and effective control signal for the long term control of an external device.

SUMMARY OF THE INVENTION

According to a first aspect of the invention, a neural interface system is disclosed. The neural interface system collects multicellular signals emanating from the central nervous system of a patient and transmits processed signals to a controlled device. The system comprises a sensor for detecting multicellular signals. The sensor may comprise a plurality of electrodes. The electrodes are designed to allow chronic detection of multicellular signals. A processing unit is designed to receive the multicellular signals from the sensor and process the multicellular signals to produce processed signals. The processed signals are transmitted from the processing unit to a controlled device. The system comprises two or more discrete components and a first discrete component transmits data or other electronic information to a second discrete component. A unique electronic identifier is embedded in one or more transmissions of the electronic information.

The two or more discrete components can be implanted in the patient or external to the patient's body. Physical cables and/or wireless communication means are utilized to transfer the electronic information from one discrete component to another. In a preferred embodiment, the unique electronic identifier is embedded in one or more discrete components of the system. In another preferred embodiment, the unique electronic identifier is embedded in all discrete components that are detachable from the system or utilize wireless transmission of electronic information.

In another preferred embodiment, the neural interface system includes a calibration module. The calibration module may include calibration routines for multiple patients, with each patient corresponding to a different unique electronic identifier.

In another preferred embodiment, the multicellular signals detected by the sensor of the system comprise one or more of neuron spikes, electrocorticogram signals, local field potential signals and electroencephalogram signals.

In another preferred embodiment, the sensor comprises one or more multi-electrode arrays with surface penetrating electrodes. The arrays are placed in one or more locations within the body of the patient, such as the motor cortex of the patient's brain. In another preferred embodiment, non-penetrating electrodes are utilized, such as in combination with penetrating electrodes, to detect multicellular signals from the brain or at extracranial locations such as the patient's scalp.

In another preferred embodiment, the discrete component includes, in whole, in part, or in combination, one or more of the following: the sensor, the processing unit, the controlled device, a display monitor, a calibration or system configuration module, a memory storage device, a telemetry device, a physical cable connecting device, a power supply module, a recharging module, an information recall and display unit and a system diagnostic unit.

In another preferred embodiment, the discrete components include operator information, such as imprinted text, color codes, bar codes, brail or other tactile patterns, or other identifiers that correlate to the unique electronic identifier to predetermine compatibility of the system. Corresponding operator information can be included on the connecting end of one or more physical cables or on multiple discrete components that transfer electronic information between each other.

In another preferred embodiment, the unique electronic identifier is programmable and can be reprogrammed or updated multiple times. In an alternative embodiment, the unique electronic identifier is programmable one time only. In another preferred embodiment, the unique electronic identifier is hardwired in one or more discrete components of the system, such as a transcutaneous connector connected to an implanted sensor with a multi-conductor cable.

In another preferred embodiment, a neural signature for a specific patient is created based on an analysis of a set of multicellular signals detected by a sensor comprising of one or more groups of electrodes. The neural signature can be compared to one or more previous neural signatures for purposes of patient identification or system compatibility confirmation. The comparison can be performed using one or more different pattern recognition algorithms including a linear filter, maximum likelihood estimator, and a neural network.

In another preferred embodiment, the neural interface system performs a discrete component compatibility check which results in the system entering an alarm state if an incompatibility is detected. The alarm state can activate an alarm transducer such as an audible alarm, visual alarm, or tactile alarm. In another preferred embodiment, when an incompatibility is identified, control of the controlled device is modified or suspended. The system compatibility check routine confirms the same unique electronic identifier is embedded in multiple discrete components. The compatibility check routine is implemented on an active basis, such as when a physical cable is attached between discrete components or a wireless transmission is initiated, or a passive basis such as on a cyclic, routine, or periodic schedule.

In another preferred embodiment, the neural interface system includes a library of system specific values that are linked to the unique electronic identifier. The values can be stored on a computer network based platform, such as a local area network (LAN), a wide area network (WAN), or the internet.

In another preferred embodiment, the neural interface system further comprises an information recall unit for retrieving the unique electronic identifier from one or more discrete components. The information recall unit can be integrated into a discrete component of the system or be a stand alone device, such as a modified personal data assistant (PDA) device.

According to another aspect of the invention, a method is disclosed for confirming discrete component compatibility of a system for collecting multicellular signals from a patient and transmitting processed signals to a controlled device. The system comprises a sensor, and the sensor may comprise a plurality of electrodes to detect the multicellular signals. The system also comprises a processing unit for receiving the multicellular signals from the sensor, for processing the multicellular signals to produce processed signals, and for transmitting the processed signals to a controlled device. The system further comprises a controlled device for receiving the processed signals. The sensor, processing unit, and controlled device are contained in two or more discrete components, and a first discrete component transmits electronic information to a second discrete component. The system further comprises a unique electronic identifier which is embedded in two or more of the discrete components. The unique electronic identifier may be used to perform a confirmation of discrete component compatibility.

According to another aspect of the invention, a system for collecting multicellular signals from a central nervous system of a patient and for transmitting processed signals to a controlled device is disclosed. The system comprises a sensor for detecting the multicellular signals, the sensor comprising of a plurality of electrodes for detection of the multicellular signals. The system also comprises a processing unit for receiving the multicellular signals, for processing the multicellular signals to produce processed signals, and for transmitting the processed signals to the controlled device. The system further comprises a controlled device for receiving the processed signals. The processing unit creates a neural signature for the patient, representing a reproducible derivative of one or more multicellular signals detected. In a preferred embodiment, the neural signature is created while the patient is presented with a visual stimulus.

According to another aspect of the invention, a system for collecting multicellular signals from a patient and for transmitting processed signals to a controlled device is disclosed. The system comprises a sensor for detecting the multicellular signals. The sensor may comprise a plurality of electrodes to detect the multicellular signals. The system further comprises a processing unit for receiving the multicellular signals from the sensor, for processing the multicellular signals to produce processed signals, and for transmitting the processed signals to the controlled device. The system further comprises a first controlled device for receiving the processed signals and a second controlled device for receiving the processed signals. In a preferred embodiment, the system includes a unique electronic identifier embedded in one or more discrete components of the system.

According to another aspect of the invention, a system for collecting multicellular signals from a first patient and for collecting multicellular signals from a second patient and for transmitting processed signals to a controlled device is disclosed. The system comprises a first sensor for detecting the multicellular signals from a first patient. The first sensor comprises a plurality of electrodes to detect the multicellular signals. The system comprises a second sensor for detecting the multicellular signals from a second patient. The second sensor comprises a plurality of electrodes to detect the multicellular signals. The system further comprises a processing unit for receiving the multicellular signals from the first sensor and the second sensor, for processing the multicellular signals to produce processed signals, and for transmitting the processed signals to the controlled device. The system further comprises a controlled device for receiving the processed signals. In a preferred embodiment, the system included a unique electronic identifier embedded in one or more discrete components of the system.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various embodiments of the present invention, and, together with the description, serve to explain the principles of the invention.

DESCRIPTION OF THE EMBODIMENTS

Figure 1:
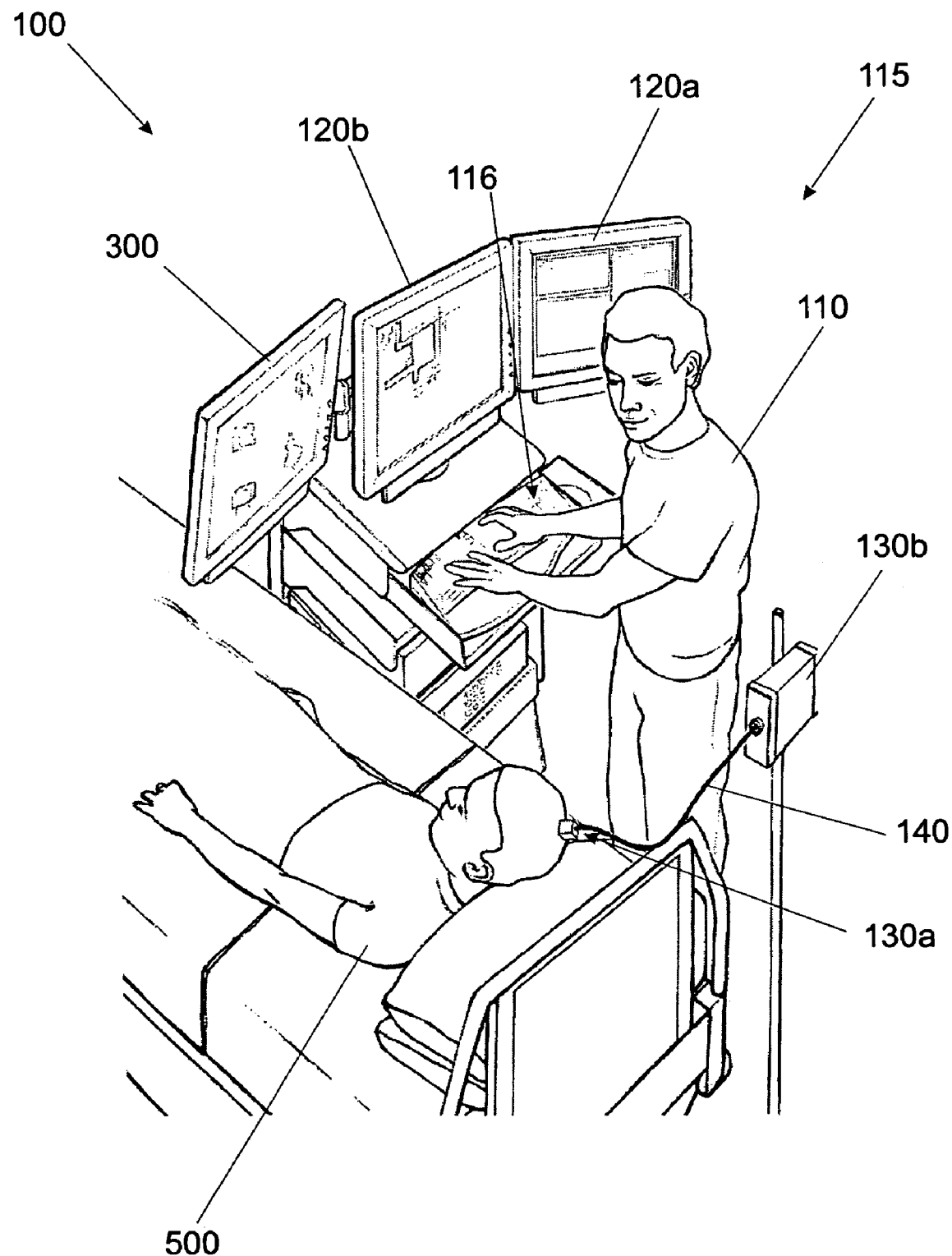
FIG. 1 illustrates a neural interface system consistent with the present invention.

Reference will now be made in detail to the present embodiments of the invention, examples of which are illustrated in the accompanying drawings. Wherever possible, the same reference numbers will be used throughout the drawings to refer to the same or like parts.

Systems and methods consistent with the invention detect neural signals generated within a patient's body and implement various signal processing techniques to generate processed signals for transmission to a device to be controlled. In one exemplary embodiment, a neural interface system includes multiple discrete components which can each transmit electronic information to a separate component through the use of a physical cable, including one or more of electrically conductive wires or optical fibers. Alternatively or additionally, transmission of data or other electronic information between discrete components can be accomplished wirelessly, by one or more discrete components including a transceiver that may transmit and receive data such as through the use of "Bluetooth" technology or according to any other type of wireless communication means, method, protocol or standard, including, for example, code division multiple access (CDMA), wireless application protocol (WAP), infrared or other optical telemetry, radiofrequency or other electromagnetic telemetry, ultrasonic telemetry, or other telemetric technology.

The system of the disclosed invention includes a sensor for detecting multicellular systems from the central nervous system of a patient. The sensor may include a plurality of electrodes that allow continual or chronic detection of the multicellular signals. A processing unit receives these multicellular signals from the sensor and utilizes various signal processing, electronic, mathematic, neural net and other techniques and processes to produce a processed signal used to control a device such as a prosthetic limb, ambulation vehicle, communication device, robot, computer or other controllable device. The system includes two or more discrete components, such as those defined by a housing or other enclosing or partially enclosing structure, or those defined as being detached or detachable from another discrete component. The discrete components of the system in their entirety include the sensor, the processing unit and the controlled device. Any one of the sensor, the processing unit and the controlled device may be only partially included in a single discrete component, and a portion of one may be included with a portion or the entirety of another in a single discrete component.

Any and all discrete components may be internal to the body of the patient, external to the body of the patient, as well as implanted in the patient but protruding through the skin such as to be accessible for connection to a physical cable. Discrete components can include, in whole or in part, numerous functions and/or components of system 100 or components to be used in combination with system 100. These discrete components include but are not limited to: a multicellular sensor, a processing unit, a controlled device, a display monitor, a calibration or system configuration module, a memory storage device, a telemetry device, a physical cable connecting device, a power supply module, a recharging module, an information recall and display unit, and a system diagnostic unit. In the instance where a discrete component includes a configuration module, the configuration module may include configuration programs, settings, and patient or system specific data for multiple patients and/or systems. In those instances, all data for a specific single system is associated, or electronically linked, with that system's unique electronic identifier. The configuration module uses the embedded unique electronic identifier during the configuration process to assure the proper data is utilized.

Electronic information or data is transmitted between one or more discrete components using one or more physical cables and/or wireless communication means. A unique electronic identifier, such as a unique alphanumeric code or serial number associated with the system, is included in one or more transmissions of electronic information between discrete components or between any discrete component and a separate device outside the system. Any and all communications that include the unique electronic identifier can be used to confirm that each discrete component is from the same or at least a compatible system. In wireless communication, the unique electronic identifier can be included in various handshaking protocols used in one or more information transmissions, such as handshaking protocols well known to those of skill in the art of wireless communication. This safety feature may be important especially as it relates to critical patient care devices such as a neural interface systems disclosed herein. For example, if a discrete component that had been calibrated or otherwise configured for use with another system or patient were accidentally attached to a discrete component of a different or otherwise incompatible system, undesired and potentially hazardous effects could occur. Thus, some exemplary embodiments of the invention may include multiple embodiments that can detect such an incompatibility to prevent undesired device control and alert the patient or other involved party of the issue.

Referring now to FIG. 1, a neural interface system 100 is shown comprising of implanted components and components external to the body of a patient 500. A sensor for detecting multicellular signals (not shown), such as a two dimensional array of multiple protruding electrodes, may be implanted in the brain of patient 500 in an area such as the motor cortex. In a preferred embodiment, the sensor is placed in an area to record multicellular signals that are under voluntary control of the patient. Alternatively or additionally, the sensor may include one or more wires or wire bundles which include a plurality of electrodes. Patient 500 of FIG. 1 is shown as a human being, but other mammals and life forms which produce recordable multicellular signals would also be applicable. Patient 500 may be a patient with a spinal cord injury or afflicted with a neurological disease that has resulted in a loss of voluntary control of various muscles within the patient's body. Alternatively or additionally, patient 500 may have lost a limb, and system 100 will include a prosthetic limb as its controlled device.

The various electrodes of the sensor detect multicellular signals, such as neuron spikes which emanate from the individual neurons of the brain. The sensor can be placed at one or more various locations within the body of patient 500, such as at an extracranial site, and preferably in a location to collect multi-cellular signals directly from the central nervous system. The electrodes can take on various shapes and forms, including the penetrating electrodes described hereabove, as well as atraumatic or blunt shapes such as those included in subdural grid electrodes or scalp electrodes. The sensor can be placed on the surface of the brain without penetrating, such as to detect local field potential (LFP) signals, or on the scalp to detect electroencephalogram (EEG) signals.

The sensor electrodes of system 100 can be used to detect various multicellular signals including neuron spikes, electrocorticogram signals (ECoG), local field potential (LFP) signals, electroencelphalogram (EEG) signals and other multicellular signals. The electrodes can detect multicellular signals from clusters of neurons and provide signals midway between single neuron and electroencephalogram recordings. Each electrode is capable of recording a combination of signals, including a plurality of neuron spikes.

A processing unit, shown in FIG. 1, comprises processing unit first portion 130a and processing unit second portion 130b. The processing unit receives the multicellular signals from the sensor and performs various signal processing functions including but not limited to amplification, filtering, sorting, conditioning, translating, interpreting, encoding, decoding, combining, extracting, mathematically transforming and/or otherwise processing those signals to generate a control signal for transmission to a controlled device. The processing unit may process signals that are mathematically combined, such as the combining neuron spikes that are first separated using spike discrimination methods known to those of skill in the art. The processing unit may include multiple components, as shown in FIG. 1, or a single component. Each of the processing unit components can be fully implanted in patient 500, be external to the body, or be implanted with a portion of the component exiting through the skin.

In FIG. 1, controlled device 300 is a computer system including a computer display with cursor control, and patient 500 may be controlling one or more of a mouse, keyboard, cursor, joystick, other computer input device, or any combinations and/or multiples of these devices. Numerous other controlled devices can be included in system 100, individually or in combination, including but not limited to prosthetic limbs, functional electrical stimulation (FES) devices and systems, robots and robotic components, teleoperated devices, computer controlled devices, communication devices, environmental control devices, vehicles such as wheelchairs, remote control devices, medical therapeutic and diagnostic equipment such as drug delivery apparatus and other controllable devices applicable to patients with some form of paralysis or diminished function as well as any device that may be better utilized under direct brain or thought control.

The sensor is connected via a multi-conductor cable, not shown, to processing unit first portion 130a which includes a transcutaneous pedestal which is mounted to the patient's skull and includes multiple conductive pads for connecting to a physical cable. The multi-conductor cable includes a separate conductor for each electrode, as well as additional conductors to serve other purposes. Various descriptions of the sensor and multi-conductor cable are described in detail in relation to subsequent figures included herebelow.

Processing unit first portion 130a may include various signal conditioning elements such as amplifiers, filters, and signal multiplexing circuitry. Processing unit first portion 130a includes a unique electronic identifier, such as a unique serial number or any alphanumeric or other retrievable, identifiable code associated uniquely with the system 100 of patient 500. The unique electronic identifier may take many different forms in processing unit first portion 130a, such as a piece of electronic information stored in a memory module; a semiconductor element or chip that can be read electronically via serial, parallel or telemetric communication; pins or other conductive parts that can be shorted or otherwise connected to each other or to a controlled impedance, voltage or ground, to create a unique code; pins or other parts that can be masked to create a binary or serial code; combinations of different impedances used to create a serial code that can be read off contacts, features that can be optically scanned and read by patterns and/or colors; mechanical patterns that can be read by mechanical or electrical detection means or by mechanical fit, radio frequency ID or other frequency spectral codes sensed by radiofrequency or electromagnetic fields, pads or other marking features that may be masked to be included or excluded to represent a serial code, or any other digital or analog codes that can be retrieved from the discrete component.

The discrete component may require power, provided internally or externally, to allow the unique electronic identifier to be retrievable, or no power may be required. Power can be supplied with numerous different forms of energy including but not limited to one or more of: acoustic energy, light energy, electromagnetic energy, electrical energy, mechanical energy and chemical energy. The unique electronic identifier can be transmitted with many different types of signals including but not limited to: acoustic signals, infrared signals, radiofrequency signals, microwave signals, optical signals and electrical signals.

In an alternative, preferred embodiment, the unique electronic identifier is a representation of one or more system parameters related to patient 500 such as the electrode impedances and/or multicellular signal shapes or amplitudes that exist after the sensor is in place, such as after having been implanted in the brain of patient 500, and potentially when the patient is presented with a particular stimulus or asked to imagine a particular event. This type of neural information, herein termed as a neural signature, is described in greater detail herebelow.

A neural signature can be used as a distinctive biometric patient identification means. Various algorithms can be used to identify a patient's identification from his brain activity including but not limited to: defining sets of electrodes that have neuron spike activity, autocorrelation shapes characterized on each electrode, firing rates on each electrode, correlation patterns between electrodes and other multicellular signal characteristics. A system could be developed to recognize a set of characteristic patterns of a patient using one or more recognition means including but not limited to: a linear filter, maximum likelihood estimator, neural network or other pattern recognition algorithm. In some exemplary embodiments, recognition of the patient's neural signature can be an active or passive part of the system 100. The recognition process could begin as soon as the patient 500 is connected via a physical cable, or a wireless transmission has been sent. The recognition process could also begin in response to another change in state. In order to create and/or check the neural signature, a stimulus, such as the flashing of a bright light, display of a picture or movie, a patient imagined movement or other imagined state or event can be used to stimulate particular multicellular signals to be generated. The specific stimulus would be repeated each time a comparative recognition process is desired, each time creating a derivative of the multicellular signals detected. The neural signature would apply to neuron spikes, LFPs, EEGs, ECoGs and other bioelectric signals.

Storage of neural signatures can be accomplished within system 100 via storage in one or more memory modules. Alternatively, separate computer systems may maintain database-like structure of neural signatures. Such databases may be maintained by service companies, supporting the neural interface systems, at hospitals and other healthcare settings, and/or at government institutions. The information can be transferred and accessed via phone lines, the internet, wireless technologies and other information transfer means. Such databases of information, whether integrated into system 100 or available at outside sources, can link neural signature information to various pieces of information, such as particular information relevant to system 100. Such information includes but is not limited to: patient calibration parameters, historic system performance, configuration and diagnostic information, controlled device calibration and other configuration settings, other patient diagnostic information gathered by system 100, and patient permissions within system 100 such as a list of useable control devices, and functional access permissions for those devices. In a preferred embodiment, these databases are under control of a caregiver, such as the clinician, which has secure control over the modification of the information.

Referring back to FIG. 1, alternatively or in addition to embedding the unique electronic identifier in processing unit first portion 130*a*, the unique electronic identifier can be embedded in the sensor and/or the multi-conductor cable connecting the sensor and processing unit first portion 130*a*. Under certain circumstances, the transcutaneous pedestal with multiple conductive pads, such as that shown embedded in processing unit first portion 130*a* of FIG. 1, may need to be replaced. Under these circumstances, a system compatibility check between a new pedestal and the remaining implanted system, the implanted sensor and/or multi-conductor cable, can be confirmed at the time of the repair or replacement surgery through the use of the embedded unique electronic identifier.

The unique electronic identifier can be embedded in one or more of the discrete components at the time of manufacture, or at a later date such as at the time of any clinical procedure involving the system, such as a surgery to implant the sensor electrodes into the brain of patient 500. Alternatively, the unique electronic identifier may be embedded in one or more of the discrete components at an even later date such as during system configuration or calibration.

Referring again to FIG. 1, processing unit first portion 130*a* is electrically attached to processing unit second portion 130*b* via intra-processing unit cable 140. Intra-processing unit cable 140, as well as other physical cables incorporated into system 100, may include electrical wires, optical fibers, other means of transmitting data and/or power and any combination of those. The number of individual conductors of intra-processing unit cable 140 can be greatly reduced from the number of conductors included in the multi-conductor cable between the implanted sensor and processing unit first portion 130*a* through signal combination circuitry included in processing unit first portion 130*a*. Intra-processing unit cable 140, as well as all other physical cables incorporated into system 100, may include shielding elements to prevent or otherwise reduce the amount of electro-magnetic noise added to the various neural signals, processed neural signals and other signals carried by those cables. In an alternative preferred embodiment, intra-processing unit cable 140 is replaced with a wireless connection for transmission between processing unit first portion 130*a* and processing unit second portion 130*b*. Wireless communication means, well known to those of skill in the art and described in more detail, can be utilized to transmit information between any of the components of system 100.

A qualified individual, operator 110, performs a calibration of system 100 at some time during the use of system 100, preferably soon after implantation of the sensor. As depicted in FIG. 1, operator 110 utilizes configuration apparatus 115 which includes two monitors, first configuration monitor 120*a* and second configuration monitor 120*b*, along with configuration keyboard 116 to perform the calibration routine and other configuration tasks such as patient training, algorithm and algorithm parameter selection, and output device setup. The software programs and hardware required to perform the calibration can be included in the processing unit, such as processing unit second portion 130*b*, or in a central processing unit incorporated into configuration apparatus 115. Configuration apparatus 115 can include additional input devices, such as a mouse or joystick, not shown. Configuration apparatus 115 can include various elements, functions and data including but not limited to: memory storage for future recall of calibration activities, operator qualification routines, standard human data, standard synthesized data, neuron spike discrimination software, operator security and access control, controlled device data, wireless communication means, remote (such as via the internet) calibration communication means and other elements, functions and data used to provide an effective and efficient calibration on a broad base of applicable patients and a broad base of applicable controlled devices. The unique electronic identifier can be embedded in one or more of the discrete components at the time of system configuration, including the act of identifying a code that was embedded into a particular discrete component at its time of manufacture, and embedding that code in a different discrete component.

Operator 110 may be a clinician, technician, caregiver or even the patient themselves in some circumstances. Multiple operators may be needed to perform a calibration, and each operator may be limited by system 100, via passwords and other control configurations, to only perform specific functions. For example, only the clinician may be able to change specific critical parameters, or set upper and lower limits on other parameters, while a caregiver, or the patient, may not be able to access those portions of the calibration procedure. The calibration procedure includes the setting of numerous parameters needed by the system 100 to properly control controlled device 300. The parameters include but are not limited to various signal conditioning parameters as well as selection and de-selection of specific multicellular signals for processing to generate the device control creating a subset of signals received from the sensor to be processed. The various signal conditioning parameters include, but are not limited to, threshold levels for amplitude sorting and filtering levels and techniques.

The operator 110 may be required by system 100 to perform certain tasks, not part of the actual calibration, to be qualified and thus allowed to perform the calibration routine. The tasks may include analysis of pre-loaded multicellular signals, either of synthetic or human data, and may include previous data captured from patient 500. The mock analysis can be tested for accuracy, requiring a minimum performance for the calibration routine to continue.

The calibration routine will result in the setting of various calibration output parameters. Calibration output parameters may include but are not limited to: electrode selection, neural signal selection, neuron spike selection, electrocorticogram signal selection, local field potential signal selection, electroencephalogram signal selection, sampling rate by signal, sampling rate by group of signals, amplification by signal, amplification by group of signals, filter parameters by signal and filter parameters by group of signals. In a preferred embodiment, the calibration output parameters are stored in memory in one or more discrete components, and the parameters are linked to the system unique electronic identifier.

Calibration routines may be performed on a periodic basis, and may include the selection and deselection of specific neural signals over time. The initial calibration routine may include initial values, or starting points, for one or more of the calibration output parameters. Subsequent calibration routines may involve utilizing previous calibration output parameters which have been stored in a memory storage element of system 100. Subsequent calibration routines may be shorter in duration than an initial calibration and may require less patient involvement. Subsequent calibration routine results may be compared to previous calibration results, and system 100 may require a repeat of calibration if certain comparative performance is not achieved.

The calibration routine may include the steps of (a) setting a preliminary set of calibration output parameters; (b) generating processed signals to control the controlled device; (c) measuring the performance of the controlled device control; and (d) modifying the calibration output parameters. The calibration routine may further include the steps of repeating steps (b) through (d).

In the performance of the calibration routine, the operator 110 may involve the patient 500 or perform steps that do not involve the patient. The operator 100 may have patient 500 think of an imagined movement, imagined state, or other imagined event, such as a memory, an emotion, the thought of being hot or cold, or other imagined event not necessarily associated with movement. The patient participation may include the use of one or more cues such as audio cues, visual cues, olfactory cues, and tactile cues. The patient 500 may be asked to imagine multiple movements, and the output parameters selected during each movement may be compared to determine an optimal set of output parameters. The imagined movements may include the movement of a part of the body, such as a limb, arm, wrist, finger, shoulder, neck, leg, ankle, and toe, and imagining moving to a location, moving at a velocity, or moving at an acceleration.

The calibration routine will utilize one or more calibration input parameters to determine the calibration output parameters. In addition to the multicellular signals themselves, system or controlled device performance criteria can be utilized. In order to optimize the system, an iterative analysis of modifying the performance criteria, based on the number of multicellular signals that meet the criteria versus the optimal number of multicellular signals to be included in the signal processing for the particular controlled device, can be performed. Criteria can be increased or decreased in the signal selection process during the calibration procedure.

Other calibration input parameters may include various properties associated with the multicellular signals, including one or more of: signal to noise ratio, frequency of signal, amplitude of signal, neuron firing rate, average neuron firing rate, standard deviation in neuron firing rate, modulation of neuron firing rate as well as a mathematical analysis of any signal property including modulation of any signal property. Additional calibration input parameters include but are not limited to: system performance criteria, controlled device electrical time constants, controlled device mechanical time constants, other controlled device criteria, types of electrodes, number of electrodes, patient activity during calibration, target number of signals required, patient disease state, patient condition, patient age and other patient parameters, and event-based (such as a patient imagined movement event) variations in signal properties including neuron firing rate activity. In a preferred embodiment, one or more calibration input parameters are stored in memory and linked to the embedded, specific, unique electronic identifier.

The calibration routine may classify one or more multicellular signals into three or more classifications for subsequent selection for further processing into the processed signal for transmission to the controlled device. The multiple classifications can be completed in the initial portion of the calibration routine, resulting in a count of each class of available signal. Based on various requirements including the requirements of the control device and applicable mathematical transfer functions, signals can be selected from the most appropriate classification, or a different number of classification states can be chosen and the signals can be reclassified in order to select the most appropriate signals for optimal device control It may be desirous for the calibration routine to exclude one or more multicellular signals based on a desire to avoid signals that respond to certain patient active functions, such as non-paralyzed functions, or even certain imagined states. The calibration routine may include having the patient imagine a particular movement or state, and based on sufficient signal activity such as firing rate or modulation of firing rate, exclude that signal from the signal processing based on that particular undesired imagined movement or imagined state. Alternatively real movement accomplished by the patient may also be utilized to exclude certain multicellular signals emanating from specific electrodes of the sensor.

Figure 2:
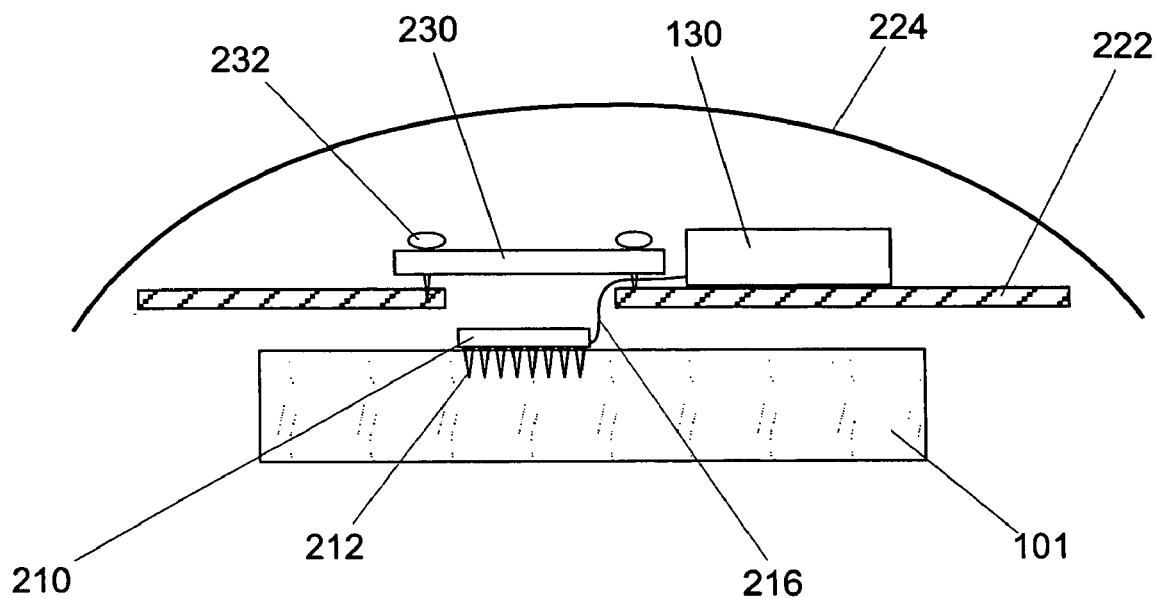
FIG. 2 illustrates an exemplary embodiment of a brain implant system consistent with the present invention.

FIG. 2 generally illustrates a brain implant system consistent with an embodiment of the present invention. As shown in FIG. 2, the system includes an electrode array 210 inserted into a patient's cerebral cortex 101 through an opening in the skull 222. Array 210 may include a plurality of electrodes 212 for detecting electrical brain signals or impulses. While FIG. 2 shows array 210 inserted into cerebral cortex 101, array 210 may be placed in any location of a patient's brain allowing for array 210 to detect electrical brain signals or impulses. Other locations for array 210, such as those outside of the cranium, can record multicellular signals as well. Non-penetrating electrode configurations, such as subdural grids, cuff electrodes and scalp electrodes are applicable both inside the cranium such as to record LFPs, in, on or near peripheral nerves, and on the surface of the scalp such as to record EEGs. Though FIG. 2 depicts the sensor as a single discrete component, in alternative embodiments, the sensor may comprise multiple discrete components. Multiple sensor components can be implanted in the brain, at an extracranial location, or any combination of locations for the multiple discrete components making up the sensor. Each discrete component can have as few as a single electrode, with the cumulative sensor containing a plurality of electrodes. Each electrode is capable of recording a plurality of neurons or other electrical activity.

Electrode array 210 serves as the sensor for the brain implant system. While FIG. 2 shows electrode array 210 as eight electrodes 212, array 210 may include one or more electrodes having a variety of sizes, lengths, shapes, forms, and arrangements. Moreover, array 210 may be a linear array (e.g., a row of electrodes) or a two-dimensional array (e.g., a matrix of rows and columns of electrodes). Each electrode 212 extends into brain 101 to detect one or more electrical neural signals generated from the neurons located in proximity to the electrode's placement within the brain. Neurons may generate such signals when, for example, the brain instructs a particular limb to move in a particular way.

In the embodiment shown in FIG. 2, each electrode 212 may be connected to a processing unit 130 via wiring 216. Processing unit 130 may be secured to skull 222 by, for example, the use of an adhesive or screws, and may even be placed inside the skull if desired. A protective plate 230 may then be secured to skull 222 underneath the surface of the patient's skin 224. In exemplary embodiments, plate 230 may be made of titanium and screwed to skull 222 using screws 232, or may comprise a section of skull 222 previously removed and attached to skull 222 using bridging straps and screws (both not shown). However, the invention may use any of a number of known protective plates, such as a biological material, and methods for attaching the same to a patients skull. Further, processing unit 130 and other surgically implanted components may be placed within a hermetically sealed housing to protect the components from biological materials. Alternative embodiments also include processing unit 130 being located external to the patient's body.

Electrodes 212 transfer the detected neural signals to processing unit 130 over wiring 216. Each projection of electrode array 210 may include a single electrode, such as an electrode at the tip of the projection, or multiple electrodes along the length of each projection. As shown in FIG. 2, wiring 216 may pass out of the opening in skull 222 beneath protective plate 230. Wiring 216, such as, for example, a multi-conductor cable connecting each electrode to processing unit 130, may then run underneath the patient's skin 224 to connect to processing unit 130. Persons skilled in the art, however, will appreciate that arrangements other than the one shown in FIG. 2 may be used to connect array 210 to processing unit 130 via wiring 216.

Processing unit 130 may preprocess the received neural signals (e.g., impedance matching, noise filtering, or amplifying), digitize them, and further process the neural signals to extract neural information that it may then transmit to an external device (not shown), such as a further processing device and/or any device to be controlled by the processed multicellular signals. For example, the external device may decode the received neural information into control signals for controlling a prosthetic limb or limb assist device, for controlling a computer cursor, or the external device may analyze the neural information for a variety of other purposes.

Processing unit 130 may also conduct adaptive processing of the received neural signals by changing one or more parameters of the system to achieve or improve performance. Examples of adaptive processing include, but are not limited to, changing a parameter during a system calibration, changing a method of encoding neural information, changing the type, subset, or amount of neural information that is processed, or changing a method of decoding neural information. Changing an encoding method may include changing neuron spike sorting methodology, calculations, thresholds, or pattern recognition. Changing a decoding methodology may include changing variables, coefficients, algorithms, and/or filter selections. Other examples of adaptive processing may include changing over time the type or combination of types of signals processed, such as EEG, LFP, neural spikes, or other signal types.

Figure 3:
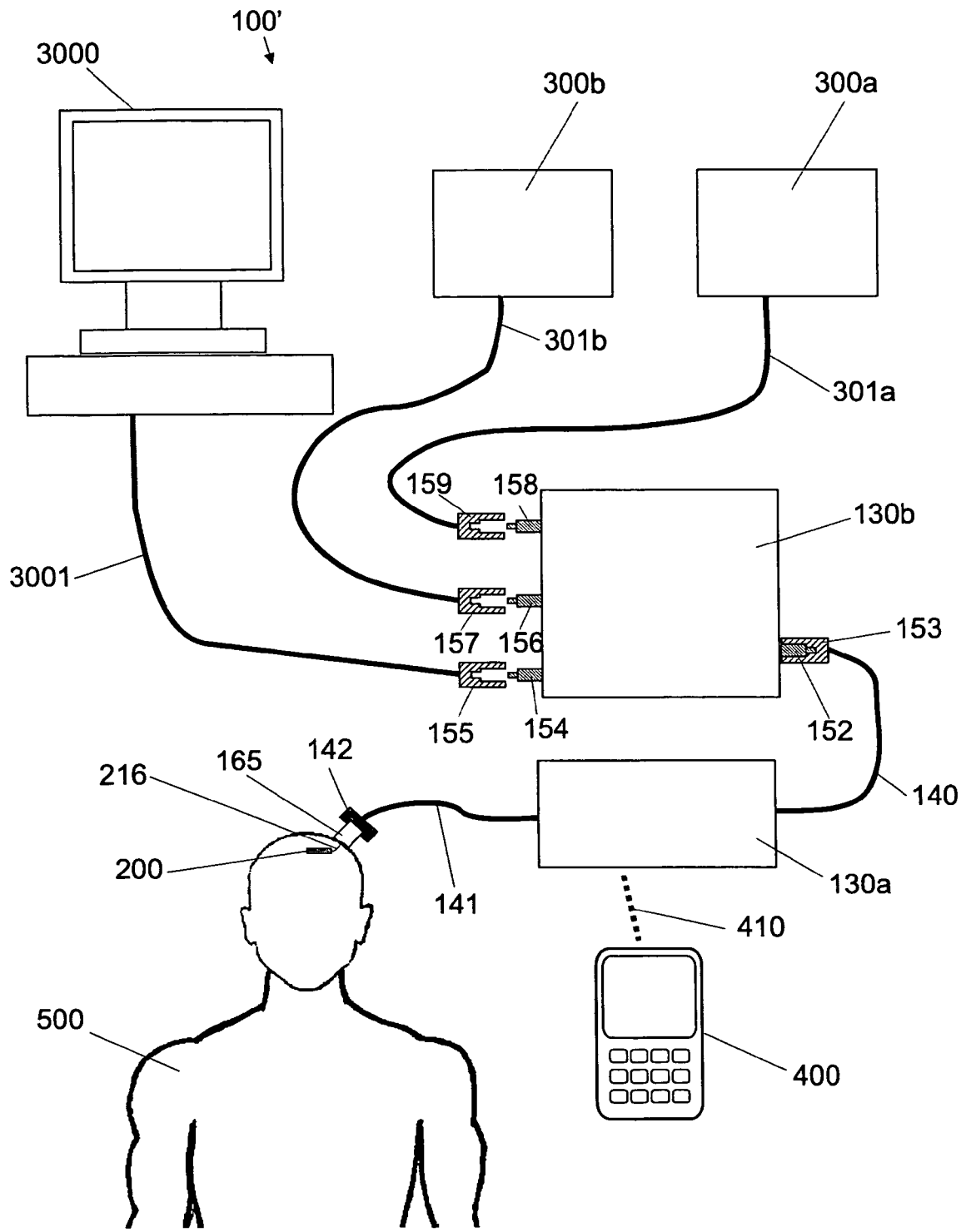
FIG. 3 illustrates another exemplary embodiment of a neural interface system consistent with the present invention wherein a single patient controls multiple devices.

Referring now to FIG. 3, a neural interface system 100' comprises implanted components and components external to the body of a patient 500. System 100' includes multiple controlled devices, controlled computer 3000, first controlled device 300a, and second controlled device 300b. While three controlled devices are depicted, this particular preferred embodiment includes any configuration of two or more controlled devices for a single patient. First controlled device 300a and second controlled device can be various types of devices such as prosthetic limbs or limb assist devices, robots or robotic devices, communication devices, computers and other controllable devices as have been described in more detail hereabove. The multiple controlled devices can include two or more joysticks, two or more computers, a robot and another controlled device, and many other combinations and multiples of devices. Each controlled device is one or more discrete components or a portion of a discrete component.

A sensor 200 for detecting multicellular signals, such as a two dimensional array of multiple protruding electrodes, may be implanted in the brain of patient 500, in an area such as the motor cortex. In a preferred embodiment, the sensor is placed in an area to record multicellular signals that are under voluntary control of the patient. Alternatively or additionally, the sensor may include one or more wires or wire bundles which include a plurality of electrodes, subdural grids, cuff electrodes, scalp electrodes, or other electrodes. Sensor 200 is attached to transcutaneous connector 165 via wiring 216, such as a multi-conductor cable including a separate conductor for each electrode of sensor 200. Transcutaneous connector 165 includes a pedestal which is screwed into the scalp of the patient, preferably in the surgical procedure in which sensor 200 is implanted in the brain of patient 500. A detachable cable, such as transcutaneous connector cable 141, attaches to transcutaneous connector 165 via transcutaneous mating plug 142. In a preferred embodiment, mating plug 142 includes amplifier circuitry, electrostatic discharge protection circuitry and/or single multiplexing circuitry such that connecting cable 141 has a reduced number of conductors as compared to wiring 216. Connector cable 141, a physical cable, is attached to processing unit first portion 130a, depicted as a permanent attachment but, in an alternative embodiment, the attachment point to processing unit first portion 130a is detachable. All of the physical cables of FIG. 3, as well as all the other figures of this disclosure, can be in a permanently attached, or detachable form. In addition, all of the physical cables included in system 100' of FIG. 3, as well as the systems of the other figures, such as transcutaneous connector cable 141, can be eliminated with the inclusion of wireless transceiver means incorporated into the applicable, communicating discrete components.

Processing unit first portion 130a, which may be a discrete component as defined in this disclosure, includes various signal processing functions as has been described in detail in relation to separate figures hereabove. Processing unit first portion 130a preferably includes a unique electronic identifier of the system, the makeup and applicability of which are described in detail hereabove. Processing unit first portion 130a electrically connects to processing unit second portion 130b via intra-processing unit cable 140. Cable 140 is detachable from processing unit second portion 130b via female plug 153 which attached to processing unit second portion 130b at its input port, male receptacle 152.

Processing unit second portion 130b includes further signal processing capability which, in combination with the signal processing of processing unit first portion 130a, produces processed signals, such as to control multiple controlled devices. As depicted in FIG. 3, controlled computer 3000, first controlled device 300a, and second controlled device 300b are controlled by the processed signals produced by processing unit first portion 130a and processing unit second portion 130b. Similar to processing unit first portion 130a, processing unit first portion 130b preferably includes the system unique electronic identifier, which can be embedded in processing unit second portion 130b at the time of manufacture, during installation procedures, during calibration or other configuration procedures, or at a later date.

The three controlled devices are shown permanently attached to physical cables, with each physical cable including a removable connection at the other end. Controlled computer 3000 is attached to controlled computer cable 3001 which has female plug 155 at its end. First controlled device 300a is attached to first controlled device cable 301a which has female plug 159 at its end. Second controlled device 300b is attached to second controlled device cable 301b which has female plug 157 at its end. Each physical cable can be attached and detached from processing unit second portion 130b. Female plug 159 attaches to male receptacle 158; female plug 157 attaches to male receptacle 156; and female plug 155 attaches to male receptacle 154.

Each of controlled computer 3000, first controlled device 300a, and second controlled device 300b preferably has embedded in it the unique electronic identifier of the system. When any of the physical cables are first attached, such as controlled computer cable 3001 being attached via female plug 157 to male receptacle 156, a compatibility check is performed by the system to assure that the unique electronic identifier embedded in controlled computer 3000 is identical or otherwise compatible with a unique electronic identifier embedded in any and all other discrete components of the system such as the unique electronic identifier embedded in processing unit second portion 130b. Similar system compatibility checks can be performed with the attachment of first controlled device 300a or second controlled device 300b. If improper compatibility is determined by the system, various actions can be taken including but not limited to: entering an alarm state, displaying incompatibility information, transmitting incompatibility information, deactivation of controlled device control, limiting controlled device control and other actions.

Also depicted in FIG. 3 is information recall unit 400 which can be used to recall and/or display the unique electronic identifier, or a surrogate, such as a more user friendly representation of the information, to an operator or other user of system 100'. The information recall unit 400 of FIG. 3 communicates with one or more discrete components of system 100' to recall the unique electronic identifier via wireless communication. In an alternative, also preferred embodiment, a physical cable attaches information recall unit 400 to one or more discrete components to recall and/or display the unique electronic identifier of that discrete component. Information recall unit 400 may include system access passwords to prevent unauthorized use, and may also include a function to set or change the unique electronic identifier of one or more discrete components of system 100'. Information recall unit 400 may have other integrated functions such as a calculator, cellular telephone, pager or personal data assistant (PDA) functions. Information recall unit 400 may be a PDA that has been modified to access system 100' to recall the unique electronic identifier of one or more components.

The information recall unit 400 of FIG. 3 includes an integrated monitor for displaying the unique electronic identifier, however in an alternative embodiment, the information recall unit can cause the unique electronic identifier to be displayed on a visualization apparatus such as the monitor of controlled computer 3000. Alternatively or additionally, the function of the information recall unit can be integrated into one or more discrete components of system 100'.

Numerous configurations and types of controlled devices can be used with system 100' of FIG. 3. Numerous types of controlled devices have been described in detail in relation to system 100 of FIG. 1 and are applicable to system 100' of FIG. 3 as well. System 100' includes a single patient 500 which can control multiple controlled devices such as controlled computer 3000, first controlled device 300a, and second controlled device 300b. While each controlled device is connected to the same discrete component, processing unit second portion 130b, in an alternative embodiment, the multiple controlled components can be connected to multiple processing unit discrete components. Also, while patient 500 may be implanted with a sensor 200 comprising a single discrete component, sensor 200 may comprise multiple discrete components, not shown, such as multiple electrode arrays, implanted in different parts of the brain, or in other various locations to detect multicellular signals. Multicellular signals from the individual sensor discrete components may be sent to individual processing units, or may be segregated in a single processing unit. Separate processed signals can be created from each individual discrete component of the sensor, and those particular signals tied to a specific controlled device. Thus, each controlled device can be controlled by processed signals from a different sensor discrete assembly, such as discrete components at different locations in the brain or other parts of the body. It should be appreciated that any combination of discrete component multicellular signals can be used in any combination of multiple controlled devices. Alternatively, whether the sensor is in a single discrete component or multiple discrete components, the processed control signals for individual controlled devices may be based on specific multicellular signals or from specific electrodes, such that individual device control is driven by specific multicellular signals. Any combination of specifically assigned signals and shared signals assigned to a controlled device are to be considered within the scope of this application.

The system 100' of FIG. 3 may include two or more separate calibration routines, such as a separate calibration routine for each controlled device. Any and all discrete components of system 100' may have a unique electronic identifier embedded in it. The processing unit of system 100' comprises processing unit first portion 130a and processing unit second portion 130b. The processing unit 100' may conduct adaptive processing as has been described in relation to the system of FIG. 2. Information transfer cables, such as the physical cables of system 100' comprising of controlled computer cable 3001, first controlled device cable 301a, second controlled device cable 301b, intra-processing unit cable 140, and transcutaneous connector cable 141 may include information such as color coded information, text information, pattern information, or other forms of visual indicators which is made available to a user connecting one or more of the physical cables in setting up the system, such that a preconfirmation of system compatibility can be performed prior to an internal system check of compatible unique electronic identifier's being present in all applicable discrete components. The visual or other information included on the physical cables can be the unique electronic identifier or a surrogate to properly match the various discrete components of system 100'. In an alternative embodiment, one or more physical cables are replaced with a wireless transceiver included in the one or more discrete components. In this preferred embodiment, compatibility information, such as text codes, bar codes, color codes and other codes can be made available to a user setting up the system. The compatibility information can be placed or otherwise made viewable on or retrievable from the discrete components which are proximally placed to support the wireless communication.

The unique electronic identifier is a unique code used to differentiate one system, such as the system of a single patient, from another system, as well as differentiate all discrete components of a system, especially detachable components, from discrete components of a separate, potentially incompatible system. The unique electronic identifier may be a random alphanumeric code, or may include information including but not limited to: patient name, other patient information, system information, implant information, number of electrodes implanted, implant location or locations, software revisions of one or more discrete components, clinician name, date of implant, date of calibration, calibration information, manufacturing codes and hospital name. In the preferred embodiment, the unique electronic identifier is stored in more than one discrete component such as a sensor discrete component and a processing unit discrete component. The unique electronic identifier may be programmable, such as one time programmable, or allow modifications for multiple time programming, such programming performed in the manufacturing of the particular discrete component, or by a user at a later date. The unique electronic identifier can be configured to be changed over time, such as after a calibration procedure. The unique electronic identifier can be permanent or semi-permanent, or hard wired, such as a hard wired configuration in a transcutaneous connector of the system. The unique electronic identifier can be used in wireless communications between discrete components, or in wireless communications between one or more discrete components and a device outside of the system.

The unique electronic identifier can represent or be linked to system status. System status can include but not be limited to: output signal characteristics, level of accuracy of output signal, output signal requirements, level of control needed, patient login settings, such as customized computer configuration information, one or more software revisions, one or more hardware revisions, controlled device compatibility list, patient permissions lists and calibration status.

The system 100' may include a library of various system data, such as data stored in electronic memory, the data being electronically linked with the unique electronic identifier. The library data may be stored in memory of one or more discrete components, such as processing unit second portion 130b. Alternatively or additionally, the library data may be stored in a computer based network platform, separate from system 100' such as a local area network (LAN), a wide area network (WAN) or the Internet. The library data can contain numerous categories of information related to the system including but not limited to: patient information such as patient name and disease state; discrete component information such as type of sensor and electrode configuration; system configuration information such as calibration dates, calibration output parameters, calibration input parameters, patient training data, signal processing methods, algorithms and associated variables, controlled device information such as controlled device use parameters and lists of controlled devices configured for use with or otherwise compatible with the system; and other system parameters useful in using, configuring, assuring safe and efficacious performance of and improving the system.

Figure 4:
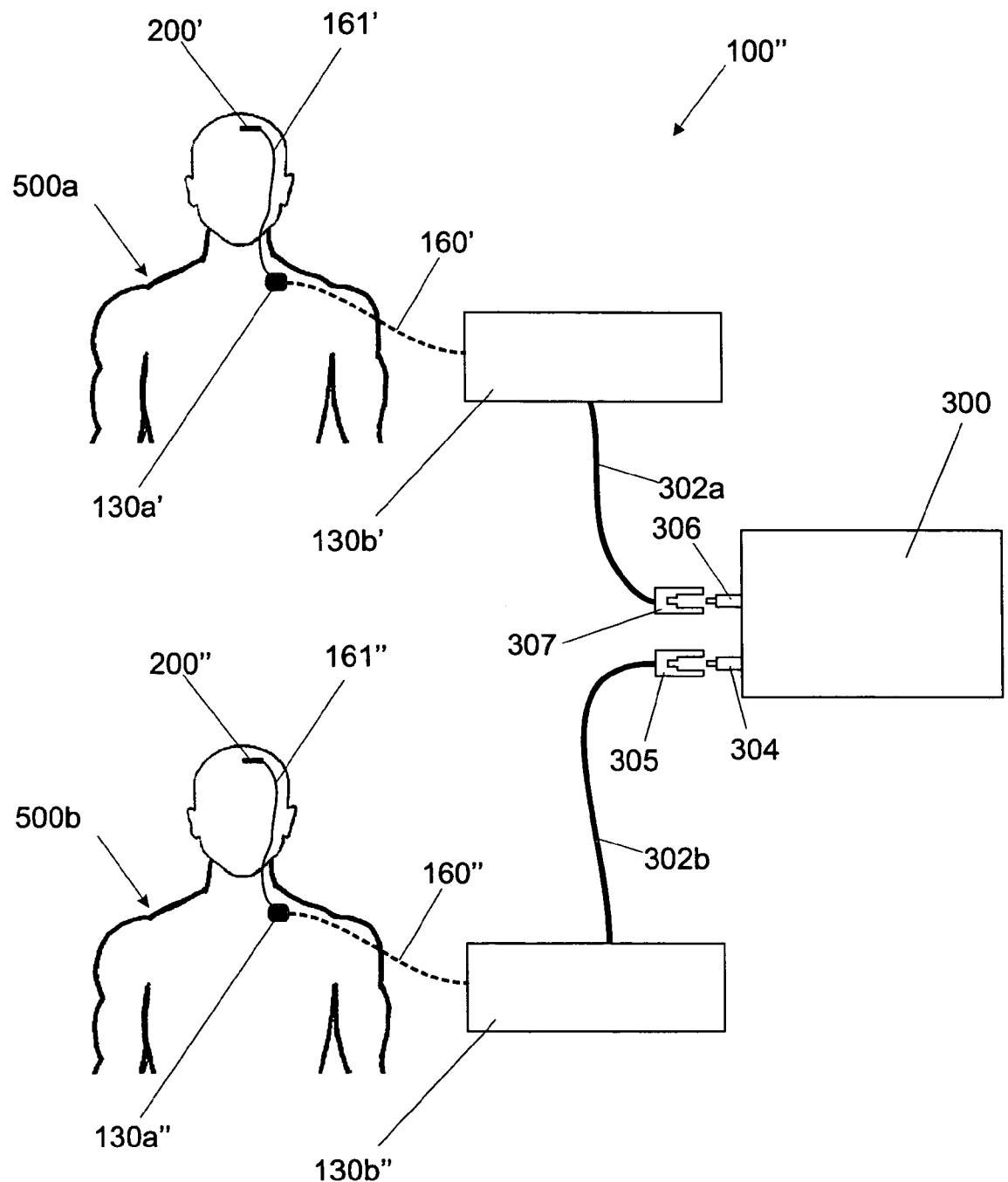
FIG. 4 illustrates another exemplary embodiment of a neural interface system consistent with the present invention wherein multiple patients control a single device.

Referring now to FIG. 4, a neural interface system 100" is shown comprising of implanted components and components external to the bodies of a first patient 500a and a second patient 500b. System 100" is a system for collecting multicellular signals from multiple patients to transmit a processed signal to one or more controlled devices. Sensors, comprising one or more discrete components, each containing one or more electrodes, detect multicellular signals from each patient. Signal processing means having one or more discrete components, are provided for processing the received multicellular signals from each patient, to produce processed signals and transmit the processed signals to the controlled device.

System 100" includes a single controlled device 300, such as a computer, a prosthetic limb, a robot, or any electronically controllable device. Numerous types of controlled devices have been described in detail in relation to system 100 of FIG. 1 and are applicable to system 100" as well. Each controlled device may comprise one or more discrete components. While a single controlled device is shown, it should be appreciated that multiple patients, such as first patient 500a and second patient 500b, can jointly control supplementary devices in addition to controlled device 300. Thus, in some exemplary embodiments, multiple patients may jointly control multiple controlled devices.

First patient 500a may be implanted in his or her brain with first sensor 200' that includes a plurality of electrodes and comprises one or more discrete components. Sensor 200' is attached to processing unit first portion 130a' via a physical cable, such as first connecting cable 161', which includes individual conductors for each electrode of sensor 200'. Processing unit first portion 130a' communicates with processing unit second portion 130b' via wireless communication means, such as first transcutaneous communication means 160', such that no implanted component passes through the skin of patient 500a. Processing unit first portion 130a' and processing unit second portion 130b' are shown as two individual discrete components, however it should be appreciated that either a single discrete component or more than two discrete components could be utilized to perform the functions of processing unit first portion 130a' and processing unit 130b'.

Similar to first patient 500a, second patient 500b may be implanted in his or her brain with second sensor 200" that includes a plurality of electrodes and comprises of one or more discrete components. Sensor 200" is attached to processing unit first portion 130a" via a physical cable, such as first connecting cable 161", which includes individual conductors for each electrode of sensor 200". Processing unit first portion 130a" communicates with processing unit second portion 130b" via wireless communication means, such as first transcutaneous communication means 160", such that no implanted component passes through the skin of patient 500b. Processing unit first portion 130a" and processing unit second portion 130b" are shown as two individual discrete components, however it should be appreciated that either a single discrete component or more than two discrete components could be utilized to perform the functions of processing unit first portion 130a" and processing unit 130b".

It should be noted that the particular design or makeup of each corresponding component of first patient 500a and second patient 500b may be exactly the same, similar or quite different. For example, processing unit first portion 130a' may include different signal processing algorithms than processing unit first portion 130a". Also, processing unit second portion 130b' may include an integrated user interface including display, keyboard and mouse, while processing unit second portion 130b" may not.

Controlled device 300 is a computer, prosthetic limb, robot or other controllable device as have been described throughout this application, and is connected to both processing unit second portion 130b' and processing unit second portion 130b" via first patient controlled device cable 302a and second patient controlled device cable 302b, respectively. First patient controlled device cable 302a is shown permanently attached at one end to processing unit second portion 130b' and includes at its other end a detachable connector, female plug 307. Female plug 307 attaches to controlled device 300 at an input port, male receptacle 306. Similarly, second patient controlled device cable 302b is shown permanently attached at one end to processing unit second portion 130b" and includes at its other end a detachable connector, female plug 305. Female plug 305 attaches to controlled device 300 at a second input port, male receptacle 304.

System 100" provides two control signals to controlled device 300. A first signal is created by detection of multicellular signals from first patient 500a via sensor 200' with signal processing conducted by processing unit first portion 130a' and processing unit second portion 130b'. A second control signal is created by detection of multicellular signals from second patient 500b via sensor 200" with signal processing conducted by processing unit first portion 130a" and processing unit second portion 130b". Controlled device 300 is configured to be controlled by two separate control signals. In an alternative, preferred embodiment, processing unit second portion 130b' and processing unit second portion 130b" are combined, such as in a single discrete component, creating a single control signal which is transmitted to a controlled device which is controlled with a single control signal.

Any and all of the discrete components of system 100" may have embedded in them a unique electronic identifier. Embedding can take the form of a hard wired or masked identifier. Alternatively or additionally, identifiers may be stored in electronic or other multiple time readable memory. Various system checks can be performed to determine that each discrete component has the same or at least a compatible unique electronic identifier. System compatibility checks can be performed on a routine, predetermined or cyclic basis, or can be triggered by a specific event such as the connection of an attachable physical cable.

Numerous methods are provided in various exemplary embodiments of the invention. An exemplary method may include a step of confirming discrete component compatibility in a system for collecting multicellular signals from a central nervous system of a patient and for transmitting processed signals to a controlled device. The system may comprise: a sensor for detecting the multicellular signals, the sensor comprising a plurality of electrodes to allow for chronic detection of the multicellular signals; a processing unit for receiving the multicellular signals from the sensor, for processing the multicellular signals to produce processed signals, and for transmitting the processed signals to the controlled device; and the controlled device for receiving the processed signals wherein the sensor, processing unit and controlled device are contained in two or more discrete components and a first discrete component transmits electronic information to a second discrete component. The system may further comprise a unique electronic identifier which is embedded in two or more of the discrete components; wherein the unique electronic identifier in said first discrete component is compared to the unique electronic identifier in said second discrete component.

The system 100" of FIG. 4 may include two or more separate calibration routines, such as a separate calibration routine for each patient. Any and all discrete components of system 100" may have a unique electronic identifier embedded in it. In a preferred embodiment, the processing units of system 100", comprising processing unit first portion 130a', processing unit second portion 130b', processing unit first portion 130a", processing unit second portion 130b", collectively or singularly conduct adaptive processing as has been described in relation to the system of FIG. 2. Information transfer cables, such as the physical cables of system 100" comprising first patient controlled device cable 302a and second patient controlled device cable 302b may include information such as color coded information, text information, pattern information or other forms of visual or other indicators which is made available to a user connecting one or more of the physical cables in setting up the system, such that a pre-confirmation of system compatibility can be performed prior to an internal system check of compatible unique electronic identifier's being present in all applicable discrete components. The information included on the physical cables can be the unique electronic identifier or a surrogate to properly match the various discrete components of system 100". In an alternative embodiment, one or more physical cables are replaced with a wireless transceiver included in the one or more discrete components. In this preferred embodiment, compatibility information, such as text codes, bar codes, color codes and other codes can be made available to a user setting up the system. The compatibility information can be placed or otherwise made viewable on or retrievable from the discrete components which are proximally placed to support the wireless communication. In another preferred embodiment, wireless communication links, such as first transcutaneous communication means 160' and second transcutaneous communication means 160" are replaced with physical cables, such as physical cables including integrated compatibility information as is described hereabove.

The unique electronic identifier is a unique code used to differentiate one system, such as a system of a multiple patients, from another system, as well as to differentiate all discrete components of a system, especially detachable components, from discrete components of a separate, potentially incompatible system. The unique electronic identifier may be a random alphanumeric code, or may include information including but not limited to: patient name, other patient information, system information, implant information, number of electrodes implanted, implant location or locations, software revisions of one or more discrete components, clinician name, date of implant, date of calibration, calibration information, manufacturing codes and hospital name. In the preferred embodiment, the unique electronic identifier is stored in more than one discrete component such as a sensor discrete component and a processing unit discrete component. The unique electronic identifier may be programmable, such as one time programmable, or allow modifications for multiple time programming, such programming performed in the manufacturing of the particular discrete component, or by a user at a later date. The unique electronic identifier can be configured to be changed over time, such as after a calibration procedure. The unique electronic identifier can be permanent or semi-permanent, or hard wired, such as a hard wired configuration in a transcutaneous connector of the system. The unique electronic identifier can be used in wireless communications between discrete components, or in wireless communications between one or more discrete components and a device outside of the system.

The unique electronic identifier can represent or be linked to system status. System status can include but not be limited to output signal characteristics, level of accuracy of output signal, output signal requirements, level of control needed, patient login settings, such as customized computer configuration information, one or more software revisions, one or more hardware revisions, controlled device compatibility list, patient permissions lists and calibration status.

The system of claim 100" may include a library of various system data, such as data stored in electronic memory, the data being electronically linked with the unique electronic identifier. The library data may be stored in memory of one or more discrete components, such as processing unit second portion 130b' or processing unit second portion 130b". Alternatively or additionally, the library data may be stored in a computer based network platform, separate from system 100" such as a local area network (LAN), a wide area network (WAN), or the Internet. The library data can contain numerous categories of information related to the system including but not limited to: patient information such as patient name and disease state; discrete component information such as type of sensor and electrode configuration; system configuration information such as calibration dates, calibration output parameters, calibration input parameters, patient training data, signal processing methods, algorithms and associated variables, controlled device information such as controlled device use parameters and lists of controlled devices configured for use with or otherwise compatible with the system; and other system parameters useful in using, configuring, assuring safe and efficacious performance of and improving the system.

It should be understood that numerous other configurations of the systems, devices, and methods described herein can be employed without departing from the spirit or scope of this application. It should be understood that the system includes multiple functional components, such as a sensor for detecting multicellular signals, a processing unit for processing the multicellular signals, and the controlled device which is controlled by the processed signals. Different from the logical components are physical or discrete components, which may include a portion of a logical component, an entire logical component and combinations of portions of logical components and entire logical components. These discrete components may communicate or transfer information to or from each other, or communicate with devices outside the system. In each system, physical wires, such as electrical wires or optical fibers, can be used to transfer information between discrete components, or wireless communication means can be utilized. Each physical cable can be permanently attached to a discrete component, or can include attachment means to allow attachment and potentially allow, but not necessarily permit, detachment. Physical cables can be permanently attached at one end, and include attachment means at the other.

The sensors of the systems of this application can take various forms, including multiple discrete component forms, such as multiple penetrating arrays which can be placed at different locations within the body of a patient. The processing units of the systems of this application can also be contained in a single discrete component or multiple discrete components, such as a system with one portion of the processing unit implanted in the patient, and a separate portion of the processing unit external to the body of the patient. Processing units may include various signal conditioning elements such as amplifiers, filters and signal multiplexing circuitry. In a preferred embodiment, an integrated spike sorting function is included. Processing units perform various signal processing functions including but not limited to: amplification, filtering, sorting, conditioning, translating, interpreting, encoding, decoding, combining, extracting, mathematically transforming and/or otherwise processing multicellular signals to generate a control signal for transmission to a controlled device. Numerous algorithms, mathematical and software techniques can be utilized by the processing unit to create the desired control signal. The processing unit may utilize neural net software routines to map neural signals into desired device control signals. Individual neural signals may be assigned to a specific use in the system. The specific use may be determined by having the patient attempt an imagined movement or other imagined state. For most applications, it is preferred that that the neural signals be under the voluntary control of the patient. The processing unit may mathematically combine various neural signals to create a processed signal for device control.

One or more discrete components of the systems of this application include a unique, readable identifier, termed a unique electronic identifier. The unique electronic identifier can be hardwired into the component, such as creating a pattern of conductors which are shorted or open circuits, a pattern of measurable impedances or voltages, or other permanent or semi-permanent, retrievable codes of information that can represent a serial number or other unique ID. Alternatively, the unique electronic identifier can be stored in a memory storage device such as electronic memory such as read only memory (ROM) or random access memory (RAM). The systems of this application can have various system checks for discrete component compatibility that can run routinely, such as on a predetermined cycle, or can be triggered by an event such as the attachment of a physical cable, or in the receiving of a wireless transmission. For wireless communication, the unique electronic identifier can be included in one or more handshaking protocols, well known to those of skill in the art, to confirm discrete component compatibility. In a preferred embodiment of each system, the system can automatically determine when a physical cable is attached, and a system compatibility check can be triggered.

In the event that a compatibility check is completed successfully, normal function of the system will commence or remain active. In the event that an incompatibility is determined, or the compatibility check otherwise fails, numerous actions can take place including but not limited to: system enters an alarm or warning state, control of controlled device is blocked, control of controlled device is partially limited and any combination of the previous. In another preferred embodiment, the cause of the incompatibility is made available to a user.

Each of the systems of this application may include various display means to display unique electronic identifier information. Each system may include an integrated alarm, or include means of activating a separate alarm system. Alarms may include one or more of audio transducers, visual elements, olfactory elements and tactile transducers. Each of the systems of this application may include integrated memory storage elements, in one or more discrete components, to store the unique electronic identifier as well as other information. Each of the systems of this application may be configured to allow remote access, such as for configuration purposes, including access via wireless means, phone lines and the internet. In remote access applications, confirmation of specific system ID, through the use of the unique electronic identifier, may prevent inadvertent configuration or other changes to a misidentified system.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for collecting multicellular signals from a central nervous system of a patient and for transmitting processed signals to a controlled device, comprising:

a sensor comprising a plurality of electrodes configured to detect the multicellular signals;

a processing unit configured to receive the multicellular signals from the sensor, process the multicellular signals to produce processed signals, and transmit the processed signals to the controlled device; and the controlled device for receiving the processed signals, wherein the processing unit creates and records a neural signature representing a reproducible derivative of one or more multicellular signals detected, and wherein a current derivative of the multicellular signals is compared to the recorded neural signature as a check for system compatibility.

2. The system of claim 1, wherein the neural signature is based on one or more of: specific channels that have spike activity, spike activity pattern shapes on multiple channels, firing rates on multiple channels, and correlation patterns between channels.

3. The system of claim 1, wherein the comparison is performed with one or more of: a linear filter, a maximum likelihood estimator, and a neural network.

4. The system of claim 1, wherein the neural signature is created while the patient is shown a specific visual stimulus.

5. The system of claim 4, wherein the current derivative of the multicellular signals is generated using the specific visual stimulus.

6. The system of claim 1, wherein the system enters an alarm state when the current derivative does not adequately match the previously recorded neural signature.

7. The system of claim 6, wherein the alarm state produces one or more of: an audible alarm, a visual alarm, and a tactile alarm.

8. A method for collecting multicellular signals from a central nervous system of a patient and for transmitting processed signals to a controlled device comprising:

detecting the multicellular signals using a sensor comprising a plurality of electrodes a processing unit receiving the multicellular signals from the sensor, processing the multicellular signals to produce processed signals, and transmitting the processed signals to the controlled device, and the controlled device receiving the processed signals, the processing unit creating and recording a neural signature representing a reproducible derivative of one or more multicellular signals detected and comparing a current derivative of the multicellular signals to the recorded neural signature as a check for system compatibility.

9. The method of claim 8, wherein the neural signature is based on one or more of: specific channels that have spike activity, spike activity pattern shapes on multiple channels, firing rates on multiple channels, and correlation patterns between channels.

10. The method of claim 8, wherein the comparing step is performed with one or more of: a linear filter, a maximum likelihood estimator, and a neural network.

11. The method of claim 8, further comprising creating the neural signature while the patient is shown a specific visual stimulus.

12. The method of claim 11, further comprising generating the current derivative of the multicellular signals using the specific visual stimulus.

13. The method of claim 8, further comprising entering an alarm state when the current derivative does not adequately match the previously recorded neural signature.

14. The method of claim 13, wherein the alarm state produces one or more of: an audible alarm, a visual alarm, and a tactile alarm.

* * * * *